(12) United States Patent
Tanikawa et al.

(10) Patent No.: US 10,136,802 B2
(45) Date of Patent: Nov. 27, 2018

(54) DEVICE FOR SUSTAINED RELEASE OF OPTICAL CLEARING AGENT, ENDOSCOPE HAVING THE SAME, AND INSTRUMENT FOR ENDOSCOPIC SURGERY HAVING THE SAME

(71) Applicant: OLYMPUS CORPORATION, Tokyo (JP)

(72) Inventors: Yohei Tanikawa, Tokyo (JP); Yasunobu Iga, Tokyo (JP); Shinichi Takimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 513 days.

(21) Appl. No.: 14/828,873

(22) Filed: Aug. 18, 2015

(65) Prior Publication Data

US 2015/0351618 A1    Dec. 10, 2015

Related U.S. Application Data

(63) Continuation of application No. PCT/JP2014/054058, filed on Feb. 20, 2014.

(30) Foreign Application Priority Data

Feb. 21, 2013   (JP) ................ 2013-032499

(51) Int. Cl.
*A61B 1/015*    (2006.01)
*A61B 1/12*    (2006.01)
(Continued)

(52) U.S. Cl.
CPC .......... *A61B 1/015* (2013.01); *A61B 1/00082* (2013.01); *A61B 1/00091* (2013.01);
(Continued)

(58) Field of Classification Search
CPC ............ A61M 2025/105; A61M 25/10; A61M 2025/1086; A61M 2025/1075;
(Continued)

(56) References Cited

U.S. PATENT DOCUMENTS 5,919,145 A * 7/1999 Sahatjian ............... A61B 10/04
                                                                                 206/363
2005/0131500 A1   6/2005 Zalesky et al.
(Continued)

FOREIGN PATENT DOCUMENTS

JP      H05-051356 A     7/1993
JP      2007-511286 A    5/2007
(Continued)

OTHER PUBLICATIONS

International Search Report dated Apr. 1, 2014 issued in PCT/JP2014/054058.
(Continued)

*Primary Examiner* — Alexandra L Newton
(74) *Attorney, Agent, or Firm* — Scully, Scott, Murphy & Presser, P.C.

(57) ABSTRACT

A device for sustained release of optical clearing agent includes a stick-shaped component having at least two supplying passages for supplying gas or liquid formed on the inside with apertures of the supplying passages being formed at positions along the circumference of the lateral surface in the vicinity of the top end of the stick-shaped component respectively, at least two pouch-shaped elastic components placed at positions along the circumference of the lateral surface in the vicinity of the top end of the stick-shaped component respectively to cover the apertures of the supplying passages respectively, an optical clearing agent holding component fixed on the surface of one of the pouch-shaped elastic components and holding optical clear-
(Continued)

ing agent, and a body-fluid absorbing component fixed on the surface of another one of the pouch-shaped elastic components and absorbing body fluid flowing from a target object or dehydrating the target object by osmotic pressure.

2 Claims, 7 Drawing Sheets

(51) Int. Cl.
*A61B 1/00* (2006.01)
*A61B 17/00* (2006.01)
*A61M 25/10* (2013.01)
*A61M 25/00* (2006.01)
*A61B 17/22* (2006.01)

(52) U.S. Cl.
CPC .......... *A61B 1/00094* (2013.01); *A61B 1/126* (2013.01); *A61B 1/128* (2013.01); *A61B 17/00234* (2013.01); *A61M 25/0026* (2013.01); *A61M 25/1011* (2013.01); *A61B 2017/00269* (2013.01); *A61B 2017/22061* (2013.01); *A61M 2025/105* (2013.01); *A61M 2025/1086* (2013.01); *A61M 2202/0468* (2013.01)

(58) Field of Classification Search
CPC .... A61M 2025/1081; A61M 2025/109; A61M 16/0481; A61M 2025/1013; A61M 2025/1031; A61B 1/00082; A61B 1/126
See application file for complete search history.

(56) References Cited

U.S. PATENT DOCUMENTS

2010/0087709 A1* 4/2010 Bertolero ........... A61B 1/00142
600/116
2012/0259401 A1* 10/2012 Gerrans ................. A61F 2/958
623/1.11

FOREIGN PATENT DOCUMENTS

| JP | 2008-188212 A | 8/2008 |
|---|---|---|
| JP | 2010-154919 A | 7/2010 |
| WO | WO 2005/049127 A1 | 6/2005 |

OTHER PUBLICATIONS

Wang, Ruikang K. et al., "Enhance light penetration in tissue for high resolution optical imaging techinques by the use of biocompatible chemical agents", Journal of X-Ray Science and Technology (2002), vol. 10, pp. 167-176.

Bashkatov, Alexey N. et al., "In vivo investigation of human skin optical clearing and blood microcirculation under the action of glucose solution", Asian Journal of Physics (2006), vol. 15, No. 1, pp. 1-14.

* cited by examiner

FIG. 6A
FIG. 6B
FIG. 6C
FIG. 6D
FIG. 6E
FIG. 6F

DEVICE FOR SUSTAINED RELEASE OF OPTICAL CLEARING AGENT, ENDOSCOPE HAVING THE SAME, AND INSTRUMENT FOR ENDOSCOPIC SURGERY HAVING THE SAME

This application is a continuation application based on International Patent Application No. PCT/JP2014/054058, filed on Feb. 20, 2014, and claims benefits of Japanese Patent Application No. 2013-032499 filed in Japan on Feb. 21, 2013, the contents of which are incorporated by this reference,

BACKGROUND OF THE INVENTION

1. Field of the Invention

This invention relates to: a device for sustained release of optical clearing agent which is used for giving an optical clearing agent to a diseased region on a luminal wall surface of a living body for example; an endoscope having the same; and an instrument for endoscopic surgery having the same.

2. Description of the Related Art

Conventional problems in endoscopic treatments which ESD (Endoscopic submucosal dissection) represents include intraoperative bleeding and postoperative bleeding.

However, an optical clearing agent capable of improving the light transmittancy for living-body by reducing light scattering has been developed in recent years.

One example of optical clearing agents is an aqueous solution acquired by adding glycerol and surfactant to urea, and this aqueous solution is applied to a living tissue to penetrate into the living tissue and then makes a penetrated region of the living tissue transparent like a jelly. Besides, the region that is made transparent by the optical clearing agent can be returned into its original state in which the penetrated region is uncleared, again, by giving a saline or the like to the penetrated region.

Optical clearing agents have been conventionally applied mainly through drop or injection, as disclosed in Non Patent Literature, Journal of X-ray Science and Technology, Vol. 10, No. 3-4, p 167-176, 2002 or Asian Journal of Physics, Vol. 15, No. 1, p 1-14, 2006 for example.

In order to reduce the risks of intraoperative bleeding and postoperative bleeding, it is desired that an optical clearing agent is applied to a diseased region before or after surgery so that vascular visibility is improved.

By the way, it is characteristic of such an optical clearing agent to take predetermined time to penetrate into a living tissue so that time lag occurs until an optical clearing effect is obtained. As a result, the optical clearing agent has to be applied to a target region with the optical clearing agent remaining at the target region, until the enough optical clearing effect is obtained.

However, a target region to which an optical clearing agent should be applied does not necessarily exist in the gravity direction in a lumen.

As a result, in a method of applying an optical clearing agent to a target region through drop, it is difficult to apply the optical clearing agent to a target region existing in the opposite direction to the gravity direction while the optical clearing agent is being kept stably remaining at the target region.

On the other hand, an optical clearing agent can be made to remain at a target region in a method of applying an optical clearing agent to a target region through injection. However, the range of a region to which the optical clearing agent is applied is extremely localized. As a result, in the case where the range of a region to which the optical clearing agent has to be applied is wide in the method of applying the optical clearing agent to the target region through injection, it not only is difficult to apply the optical clearing agent to the whole range of the desired region from an injection point but also has a high invation for living tissue.

However, for example, Patent literature, Japanese Patent Kokai No. 2008-188212, offers an agent-applying instrument that is used with the aim of applying an anesthetic to nasal cavity. This agent-applying instrument can be used for applying an agent to a wide range of a diseased region with low invasion with the agent kept stably remaining at the diseased region.

The agent-applying instrument disclosed in Japanese Patent Kokai No. 2008-188212 includes: an elongated stick-shaped base components 51; a gas passage 52 running along the base component; a cylinder-shaped balloon 53 placed on the whole circumference of the outside surface of the base component 51 and communicating with the gas passage 52; and an agent-holding component 54 placed on the outside surface of the balloon 53 and containing an agent that is applied to the body cavity, as shown in FIG. 8. And, the agent-applying instrument disclosed in Patent literature 1 is configured to apply an anesthetic to a desired region by supplying air to the gas passage 52 with a gas-supplying instrument to inflate the balloon 53 so that the agent-holding component 54 presses on the inside surface of the desired region to come into contact with the desired region.

SUMMARY OF THE INVENTION

A device for sustained release of optical clearing agent according to the present invention is characterized in that the device includes: a stick-shaped component which includes at least two supplying passages for supplying gas or liquid, the supplying passages being formed on the inside of the stick-shaped component, and which includes apertures of the respective supplying passages, the apertures being formed at positions along the circumference of the lateral surface in the vicinity of the top end of the stick-shaped component respectively; at least two pouch-shaped elastic components which are placed at positions along the circumference of the lateral surface in the vicinity of the top end of the stick-shaped component respectively to cover the apertures of the supplying passages respectively and which can be controlled to inflate or deflate in accordance with an amount of an inflow of or an outflow of the gas or liquid; an optical clearing agent holding component which is fixed on the surface of a first component of the pouch-shaped elastic components, which holds optical clearing agent, and which is pressed to perform sustained release of the optical clearing agent to the outside; and a body-fluid absorbing component which is fixed on the surface of a second component of the pouch-shaped elastic components and which absorbs body fluid flowing from a target object for sustained release of the optical clearing agent or dehydrates the target object by osmotic pressure.

Also, in a device for sustained release of optical clearing agent according to the present invention, it is preferred that the part in the vicinity of the top end of the stick-shaped component, which includes at least two pouch-shaped elastic components, is configured to be capable of rotating on an axis of the stick-shaped component.

Also, in a device for sustained release of optical clearing agent according to the present invention, it is preferred that the optical clearing agent holding component includes innumerable protuberances which are formed on its surface.

Also, in a device for sustained release of optical clearing agent according to the present invention, it is preferred that the device includes a penetration-rate adjusting element which increases a rate at which the optical clearing agent held by the optical clearing agent holding component penetrates into the target object.

Also, in a device for sustained release of optical clearing agent according to the present invention, it is preferred that the penetration-rate adjusting element is a temperature adjusting apparatus which heats gas or liquid supplied to the first pouch-shaped elastic component.

Also, in a device for sustained release of optical clearing agent according to the present invention, it is preferred that the penetration-rate adjusting element is a penetration-rate accelerating agent which mixes with the optical clearing agent held by the optical clearing agent holding component.

Also, in a device for sustained release of optical clearing agent according to the present invention, it is preferred that: the stick-shaped component includes a third supplying passage for supplying gas or liquid with an aperture of the third supplying passage formed at a position along the circumference of the lateral surface in the vicinity of the top end of the stick-shaped component, the third supplying passage being formed on the inside of the stick-shaped component; and the device for sustained release of optical clearing agent includes an optical clearing effect-cancelling agent holding component which is fixed on a surface of a third pouch-shaped elastic component, which holds liquid for returning the living tissue made transparent into its original state in which the living tissue is uncleared, and which is pressed to perform sustained release of the liquid for returning the living tissue made transparent into its original uncleared state of the living tissue to the outside, the third pouch-shaped elastic component being placed at a position along the circumference of the lateral surface in the vicinity of the top end of the stick-shaped component to cover the aperture of the third supplying passage while the position of the third pouch-shaped elastic component placed is being different from the positions of the first pouch-shaped elastic component and the second pouch-shaped elastic component placed respectively, and the third pouch-shaped elastic component being capable of being controlled to inflate and deflate in accordance with an amount of inflow of or outflow of the gas or liquid.

Also, in a device for sustained release of optical clearing agent according to the present invention, it is preferred that the stick-shaped component further includes a supplying passage for supplying the optical clearing agent which communicates with the optical clearing agent holding component.

Also, an endoscope according to the present invention includes one of the above-described device for sustained release of optical clearing agent of the present invention.

Also, an instrument for endoscopic surgery according to the present invention includes one of the above-described device for sustained release of optical clearing agent of the present invention.

These and other features and advantages of the present invention will become apparent from the following detailed description of the preferred embodiments when taken in conjunction with the accompanying drawings.

BRIEF DESCRIPTION OF THE DRAWINGS

FIG. 1A is a side view showing an appearance of a state in which the pouch-shaped elastic components are not inflated, FIG. 1B is a cross-sectional view taken along a line A-A in FIG. 1A, FIG. 1C is a cross-sectional view taken in the direction parallel to the plane of the paper sheet showing FIG. 1A, and FIG. 1D is a cross-sectional view showing a state in which the pouch-shaped elastic components are inflated, FIG. 1D being taken in the direction parallel to the plane of the paper sheet showing FIG. 1A.

FIGS. 2A to 2D are explanatory views showing an example of a procedure for sustained release of optical clearing agent with the device for sustained release of optical clearing agent of the first embodiment while FIGS. 2B to 2D are being illustrated as a cross-sectional view taken in the direction parallel to the plane of paper sheet showing FIG. 2A, FIG. 2A is a view showing a state in which: the device for sustained release of optical clearing agent is inserted into a lumen with none of the pouch-shaped elastic components inflated; and then position adjustment for the body-fluid absorbing component is performed so that the body-fluid absorbing component faces a target region for sustained release of optical clearing agent, FIG. 2B is a view showing a state in which the second pouch-shaped elastic component is inflated from the state shown in FIG. 2A to press the body-fluid absorbing component to the target region so that the body-fluid absorbing component comes into contact with the target region, FIG. 2C is a view showing a state in which: the second pouch-shaped elastic component is deflated from the state shown in FIG. 2B; and then a part in the vicinity of the top end of the stick-shaped component is rotated on the axis of the stick-shaped component so that the optical clearing agent holding component faces the target region, and FIG. 2D is a view showing a state in which the first pouch-shaped elastic component is inflated from the state shown in FIG. 2C to press the optical clearing agent holding component to the target region so that the optical clearing agent holding component comes into contact with the target region.

FIG. 3A is a partially enlarged cross-sectional view showing the surface shape of the optical clearing agent holding component, FIG. 3B is a view showing an area which the optical clearing agent holding component for the device for sustained release of optical clearing agent of the second embodiment shown in FIG. 3A occupies, FIG. 3C is a view showing a state in which the optical clearing agent holding component is pressed to a target region for sustained release of optical clearing agent so that the optical clearing agent holding component comes into contact with the target region, FIG. 3D is a view showing: the shape of the pressed contact surface of the target region for sustained release of optical clearing agent in the range of the area shown in FIG. 3C; and a position in the direction in which the optical clearing agent holding component is pressed to come into contact with the target region, when the optical clearing agent holding component is pressed to the target region to come into contact with the target region through the device for sustained release of optical clearing agent of the second embodiment, and FIG. 3E is a view showing one example for comparison with the optical clearing agent holding component shown in FIG. 3D and showing: the shape of the pressed contact surface of the target region for sustained release of optical clearing agent in the range of the area shown in FIG. 3C; and a position in the direction in which an optical clearing agent holding component having a smooth surface is pressed to come into contact with the target region, when the optical clearing agent holding component having a smooth surface is pressed to the target region to come into contact with the target region.

FIG. 5A is a side view showing an appearance of a state in which the pouch-shaped elastic components are not inflated, FIG. 5B is a cross-sectional view taken along a line A'-A' in FIG. 5A, and FIG. 5C is a cross-sectional view taken in the direction parallel to the plane of the paper sheet showing FIG. 5A.

FIGS. 6A to 6F are explanatory views showing an example of a procedure for sustained release of optical clearing agent with the device for sustained release of optical clearing agent of the fourth embodiment according to the present invention while FIGS. 6B to 6F are being illustrated as a cross-sectional view taken in the direction parallel to the plane of paper sheet showing FIG. 6A, FIG. 6A is a view showing a state in which: the device for sustained release of optical clearing agent is inserted into a lumen with none of the pouch-shaped elastic components inflated; and then the position adjustment for body-fluid absorbing component is performed so that the body-fluid absorbing component faces a target region for sustained release of optical clearing agent, FIG. 6B is a view showing a state in which the second pouch-shaped elastic component is inflated from the state shown in FIG. 6A to press the body-fluid absorbing component to the target region so that the body-fluid absorbing component comes into contact with the target region, FIG. 6C is a view showing a state in which: the second pouch-shaped elastic component is deflated from the state shown in FIG. 6B; and then a part in the vicinity of the top end of the stick-shaped component is rotated on the axis of the stick-shaped component so that the optical clearing agent holding component faces the target region, FIG. 6D is a view showing a state in which the first pouch-shaped elastic component is inflated from the state shown in FIG. 6C to press the optical clearing agent holding component to the target region so that the optical clearing agent holding component comes into contact with the target region, FIG. 6E is a view showing a state in which: the first pouch-shaped elastic component is deflated from the state shown in FIG. 6D; and then the part in the vicinity of the top end of the stick-shaped component is rotated on the axis of the stick-shaped component so that the optical clearing effect-cancelling agent holding component faces the target region, and FIG. 6F is a view showing a state in which the third pouch-shaped elastic component is inflated from the state shown in FIG. 6E to press the optical clearing effect-cancelling agent holding component to the target region so that the optical clearing effect-cancelling agent holding component comes into contact with the target region.

DETAILED DESCRIPTION OF THE PREFERRED EMBODIMENTS

Figure 1A:
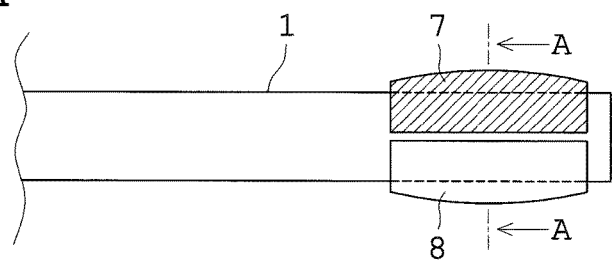
FIGS. 1A to 1D are explanatory views schematically showing a sketchy structure of a device for sustained release of optical clearing agent of the first embodiment according to the present invention.

Prior to the explanation of embodiments of the present invention, operation effects of the present invention are explained.

A luminal wall surface of a living body which is a target for sustained release of optical clearing agent is covered in body fluid. Also, there exists much body fluid in the upper layer of the living tissue which has to be made transparent, also on the inside of the luminal wall surface. When much body fluid mixes with an optical clearing agent, the optical clearing agent is diluted, so that the function of the optical clearing agent making a living tissue transparent deteriorates and penetration of the optical clearing agent into the living tissue that is required to become transparent is retarded. In order to shorten necessary time for obtaining the enough optical clearing effect by sustained release of the optical clearing agent to the luminal wall surface, the living tissue being required to become transparent, the body fluid existing on the surface of or on the inside of the luminal wall surface has to be reduced to the utmost so that the optical clearing agent easily penetrates into the living tissue that is required to become transparent.

In addition, it is important to reduce physical burden on the living tissue to the utmost also in an operation for shortening time necessary for sustained release of optical clearing agent to the luminal wall surface.

Accordingly, as in the present invention, a device for sustained release of optical clearing agent according to the present invention includes: a stick-shaped component which includes at least two supplying passages for supplying gas or liquid and apertures of the respective supplying passage, the supplying passage being located on the inside of the stick-shaped component, and the apertures being located at positions along the circumference of the lateral surface in the vicinity of the top end of the stick-shaped component; at least two pouch-shaped elastic components which are placed at positions along the circumference of the lateral surface in the vicinity of the top end of the stick-shaped component respectively to cover the apertures of the supplying passages respectively and which can be controlled to inflate or deflate in accordance with an amount of inflow of or outflow of the gas or liquid; an optical clearing agent holding component which is fixed on the surface of a first component of the pouch-shaped elastic components, which holds an optical clearing agent, and which is pressed to sustainedly release the optical clearing agent to the outside; and a body-fluid absorbing component which is fixed on the surface of a second component of the pouch-shaped elastic components, and which absorbs body fluid flowing from a target object for sustained release of optical clearing agent or dehydrates the target object by osmotic pressure. As a result, sustained release of the optical clearing agent to the luminal wall surface can be performed by the optical clearing agent holding component while the body-fluid absorbing component is removing body fluid adhering to the luminal wall surface to reduce an amount of body fluid in a surface layer of the inside of the luminal wall surface to the utmost. As a result, an amount of body fluid mixing with the optical clearing agent can be reduced to the utmost, so that it is possible to shorten time which the optical clearing agent needs to penetrate into a living tissue that is required to become transparent in the luminal wall surface.

In addition, as in a device for sustained release of optical clearing agent according to the present invention, the body-fluid absorbing component and the optical clearing agent holding component are placed at positions along the circumference of the lateral surface in the vicinity of the top end of the stick-shaped component respectively. As a result, absorption of body fluid by the body-fluid absorbing component and sustained release of the optical clearing agent by the optical clearing agent holding component can be changed to each other to perform the absorption of body fluid or the sustained release of the optical clearing agent without inserting or pulling the stick-shaped component into or out of the living body, by rotating on the axis of the stick-shaped component the part in the vicinity of the top end of the stick-shaped component on which the fluid-body absorbing component and the optical clearing agent holding component are placed, so that a physical burden on the living body and work burden can be reduced to the utmost.

In addition, as in the device for sustained release of optical clearing agent according to the present invention, the optical clearing agent holding component and the body-fluid absorbing component are fixed on the pouch-shaped elastic components respectively. As a result, the optical clearing agent holding component and the body-fluid absorbing component can be pressed to come into contact with the luminal wall surface of the target region by inflating the pouch-shaped elastic components respectively, so that also a target region existing in the opposite direction to the direction of gravity can be stably given the optical clearing agent and body fluid can be stably removed from also the target region existing in the opposite direction to the direction of gravity.

Accordingly, such a constitution as in the device for sustained release of optical clearing agent according to the present invention: makes it possible to shorten necessary time for obtaining the optical clearing effect by the optical clearing agent to the utmost with a physical burden on a living body and a work burden reduced; and, in addition, makes it possible to stably gives an optical clearing agent to also a target region for administration of optical clearing agent which exists in the opposite direction to the direction of gravity.

Also, when a part in the vicinity of the top end of the stick-shaped component which is provided with the at least two pouch-shaped elastic components is configured to be capable of being rotated on the axis of the stick-shaped component in a device for sustained release of optical clearing agent according to the present invention, absorption of body fluid by the body-fluid absorbing component and sustained release of optical clearing agent by the optical clearing agent holding component can be changed to each other to perform absorption of body fluid or sustained release of optical clearing agent without inserting or pulling the stick-shaped component into or out of a living tissue. As a result, it is possible to realize the effect of reducing a physical burden on the living body and work burden to the utmost.

Also, when the optical clearing agent holding component includes innumerable protuberances formed on its surface in a device for sustained release of optical clearing agent according to the present invention, the protuberances press against the surface of a target region for sustained release of optical clearing agent in the case where the optical clearing agent holding component is pressed to the target object, so that the shape of the surface of the target region is deformed into a bumpy shape corresponding to the protuberances of the optical clearing agent holding component. As a result, the surface area of the target region into which optical clearing agent penetrates remarkably increases. In addition, the optical clearing agent holding component can be made to enter the target region for sustained release of optical clearing agent all the more inside because the shape of the surface of the target region for sustained release of optical clearing agent is deformed into the bumpy shape by the protuberances of the optical clearing agent holding component, so that the distance between: the optical clearing agent; and the living tissue that is required to be made transparent and that exists on the inside of the target region for sustained release of optical clearing agent can be shortened. As a result, it is possible to remarkably shorten necessary time for making the living tissue transparent, the living tissue being required to be transparent and existing on the inside of the target region for sustained release of optical clearing agent, because: more optical clearing agent can be applied to the target region for sustained release of optical clearing agent; and the distance between: the optical clearing agent penetrating into the target region; and the living tissue required to be transparent and existing on the inside of the target region for sustained release of the optical clearing agent can be shortened.

Also, when a device for sustained release of optical clearing agent according to the present invention includes a penetration-rate adjusting element which increases a rate at which the optical clearing agent held by the optical clearing agent holding component penetrates into a target tissue for sustained release of optical clearing agent, it is possible to accelerate dehydration of body fluid from the target tissue. Accordingly, when the optical clearing agent holding component is configured in such a way that the surface of the optical clearing agent holding component discharges the optical clearing agent to the outside whereas the surface of the optical clearing agent holding component does not allows body fluid passing through the surface, the body fluid from the target region is dehydrated by the optical clearing agent discharged from the surface of the optical clearing agent holding component and, afterward, body fluid flowing from the target region is absorbed by the body-fluid absorbing component. And then, the optical clearing agent holding component is made to press again on the target region in which an amount of the body fluid was reduced, to come into contact with the target region. As a result, the optical clearing agent discharged from the optical clearing agent holding component can easily penetrate into the inside of the target region. As a result, it is possible to shorten necessary time for making the living tissue transparent all the more, the living tissue being required to become transparent and existing on the inside of the target region for sustained release of optical clearing agent.

Also, when the penetration-rate adjusting element is composed of a temperature adjusting apparatus which heats gas or liquid that is supplied to the first pouch-shaped elastic component in a device for sustained release of optical clearing agent according to the present invention, it is possible to shorten necessary time for making the living tissue transparent all the more, the living tissue being required to become transparent and existing on the inside of the target tissue for sustained release of optical clearing agent. In addition, it becomes easy to adjust necessary time for making the living tissue transparent.

Also, when the penetration-rate adjusting element is a penetration-rate accelerating agent which mixes with the optical clearing agent held by the optical clearing agent holding component in a device for sustained release of optical clearing agent according to the present invention, it is possible to shorten necessary time for making the living tissue transparent all the more, the living tissue being required to be transparent and existing on the inside of the target region for sustained release of optical clearing agent.

Also, a device for sustained release of optical clearing agent according to the present invention is configured in such a way that: the stick-shaped component includes a third supplying passage for supplying gas or liquid with an aperture of the third supplying passage located at a position along the circumference of the lateral surface in the vicinity of the top end of the stick-shaped component, the third supplying passage being formed on the inside of the stick-shaped component; a third pouch-shaped elastic component is placed at a position along the circumference of the lateral surface in the vicinity of the top end of the stick-shaped component to cover the aperture of the third supplying passage while the position of the third pouch-shaped elastic component placed is differing from the positions of the first pouch-shaped elastic component and the second pouch-shaped elastic component placed respectively, the third pouch-shaped elastic component being capable of being controlled to inflate or deflate in accordance with an amount of inflow of or outflow of the gas or liquid; and the device for sustained release of optical clearing agent includes an optical clearing effect-cancelling agent holding component which is fixed on the surface of the third pouch-shaped elastic component, which holds an agent for retuning the living tissue made transparent into its original state in which the living tissue is uncleared, and which is pressed to sustainedly release to the outside the agent for returning the living tissue made transparent into its original uncleared state. Such a constitution not only makes it possible to shorten time which the optical clearing agent needs to penetrate into the living tissue which is required to become transparent and which exists on the inside of a diseased region on the luminal wall surface by sustainedly releasing the optical clearing agent by the optical clearing agent holding component while an amount of body fluid existing on the surface of or in the surface layer on the inside of the diseased region on the luminal wall surface is being reduced to the utmost by the body-fluid absorbing component but also makes it possible to stably apply the optical clearing effect-cancelling agent to also a target region for sustained release existing in the opposite direction to the direction of gravity without inserting and pulling the stick-shaped component into or out of the living body also in a process of unclearing the living tissue having been made transparent, so that it is possible to reduce a physical burden on the living body and a work burden all the more.

Also, when the stick-shaped component further includes an optical clearing agent supplying passage which communicates with the optical clearing agent holding component in a device for sustained release of optical clearing agent according to the present invention, it is possible to control an amount of the optical clearing agent sustainedly released to the target region for sustained release of optical clearing agent into a suitable amount. As a result, even in the case where an amount of the optical clearing agent necessary for making the living tissue existing in the target region transparent exceeds an amount of the optical clearing agent which can be held by the optical clearing agent holding component and additional sustained release of the optical clearing agent is needed, another amount of the optical clearing agent can be properly supplied to the optical clearing agent holding component through the optical clearing agent supplying passage as necessary, so that it is possible to complete the process of making the living tissue transparent without pulling the stick-shaped component out of the living body.

Also, as in the present invention, when an endoscope and an instrument for endoscopic surgery include one of the above-described device for sustained release of optical clearing agent according to the present invention, it is possible to realize an endoscope and an instrument for endoscopic surgery which have the effects of the above described device for sustained release of optical clearing agent according to the present invention.

Embodiments of the present invention are explained using the drawings, below.

First Embodiment

Figure 1B:
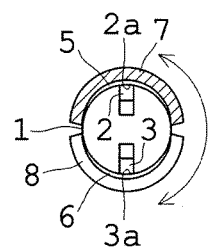
Figure 1C:
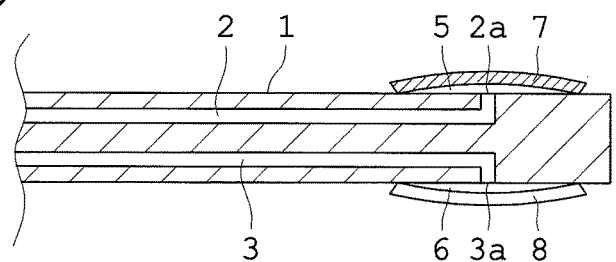
Figure 1D:
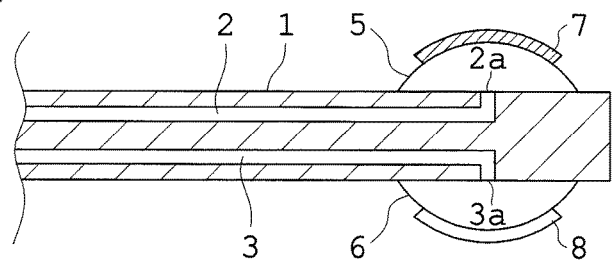
Figure 2A:
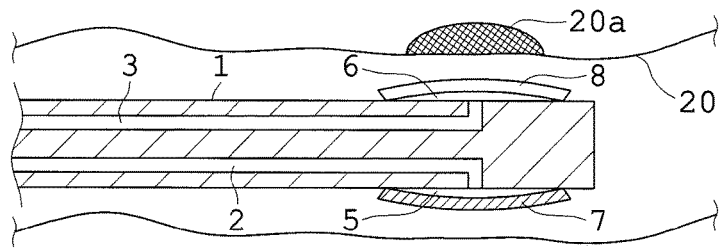
Figure 2B:
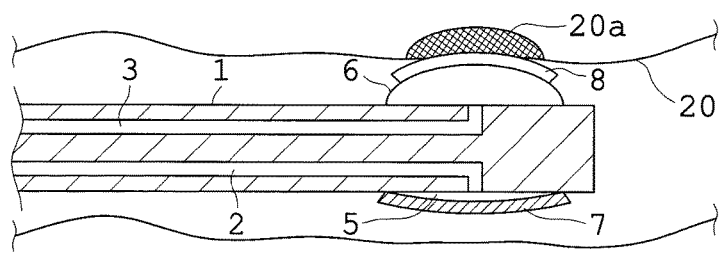
Figure 2C:
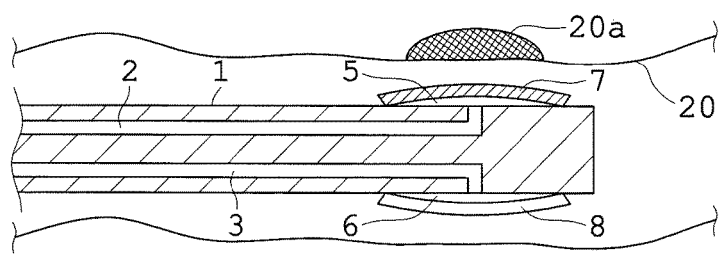
Figure 2D:
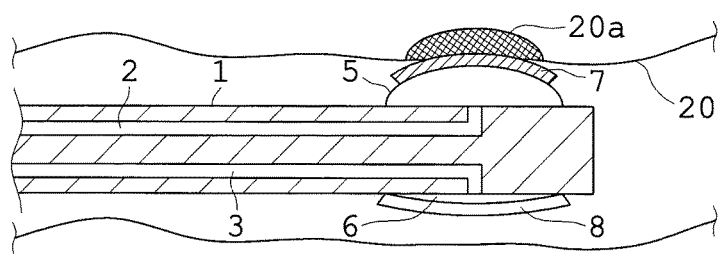

FIGS. 1A to 1D are explanatory views schematically showing a sketchy structure of a device for sustained release of optical clearing agent of the first embodiment according to the present invention, FIG. 1A is a side view showing an appearance of a state in which the pouch-shaped elastic components are not inflated, FIG. 1B is a cross-sectional view taken along a line A-A in FIG. 1A, FIG. 1C is a cross-sectional view taken in the direction parallel to the plane of the paper sheet showing FIG. 1A, and FIG. 1D is a cross-sectional view showing a state in which the pouch-shaped elastic components are inflated, FIG. 1D being taken in the direction parallel to the plane of the paper sheet showing FIG. 1A. FIGS. 2A to 2D are explanatory views showing an example of a procedure for sustained release of optical clearing agent with the device for sustained release of optical clearing agent of the first embodiment while FIGS. 2B to 2C are being illustrated as a cross-sectional view taken in the direction parallel to the plane of paper sheet showing FIG. 2A, FIG. 2A is a view showing a state in which: the device for sustained release of optical clearing agent is inserted into a lumen with none of the pouch-shaped elastic components inflated; and then position adjustment for the body-fluid absorbing component is performed so that the body-fluid absorbing component faces a target region for sustained release of optical clearing agent, FIG. 2B is a view showing a state in which the second pouch-shaped elastic component is inflated from the state shown in FIG. 2A to press the body-fluid absorbing component to the target region so that the body-fluid absorbing component comes into contact with the target region, FIG. 2C is a view showing a state in which: the second pouch-shaped elastic component is deflated from the state shown in FIG. 2B; and then a part in the vicinity of the top end of the stick-shaped component is rotated on the axis of the stick-shaped component so that the optical clearing agent holding component faces the target region, and FIG. 2D is a view showing a state in which the first pouch-shaped elastic component is inflated from the state shown in FIG. 2C to press the optical clearing agent holding component to the target region so that the optical clearing agent holding component comes into contact with the target region.

A device for sustained release of optical clearing agent of the present embodiment includes a stick-shaped component 1, pouch-shaped elastic components 5 and 6 which are capable of being inflated, an optical clearing agent holding component 7, and a body-fluid absorbing component 8, as shown in FIGS. 1A to 1D.

The stick-shaped component 1 is made of a flexible material and includes supplying passages 2 and 3 for supplying gas or liquid, the supplying passages 2 and 3 being formed on the inside of the stick-shaped component 1.

Also, the stick-shaped component 1 includes apertures 2a and 3a of the supplying passages 2 and 3, the apertures 2a and 3a being formed at positions along the circumference of the lateral surface in the vicinity of the top end of the stick-shaped component 1, as shown in FIG. 1B.

The supplying passages 2 and 3 connect with a unit for supplying and discharging gas or liquid for which a pump or the like is used, and the unit for supplying and discharging gas or liquid being not shown in the drawings.

The pouch-shaped elastic components 5 and 6 are composed of balloons respectively, for example. And, the pouch-shaped elastic components 5 and 6 are placed at positions along the circumference of the lateral surface in the vicinity of the top end of the stick-shaped component 1 respectively to cover the apertures 2a and 3a of the respective supplying passages 2 and 3, as shown in FIGS. 1B and 1C.

And, the balloons 5 and 6: are inflated (expand) when gas or liquid is supplied to the insides of the balloons 5 and 6 through the supplying passages 2 and 3 connecting with the unit for supplying and discharging gas or liquid which is not shown in the drawings (refer to FIG. 1D); and are deflated (contract) when gas or liquid is discharged from the insides of the balloons 5 and 6 through the supplying passages 2 and 3 (refer to FIG. 1C). Accordingly, the device for sustained release of optical clearing agent is configured to be capable of controlling inflation of and deflation of the balloons in accordance with an amount of inflow of or outflow of gas or liquid.

The optical clearing agent holding component 7 is fixed on the surface of the balloon 5 and is composed of: a sponge-like component; or a pouch-shaped component having minute holes on the surface of the pouch-shaped component to hold an optical clearing agent inside, for example. And, the optical clearing agent holding component 7 is configured to be pressed to sustainedly release the optical clearing agent to the outside.

The body-fluid absorbing component 8 is fixed on the surface of the balloon 6 and is composed of: a fiber component like gauze or absorbent cotton which absorbs body fluid from a target region for sustained release of optical clearing agent; or a dehydration sheet which dehydrates the target region for sustained release of optical clearing agent by osmotic pressure, for example.

Also, the stick-shaped component 1 is configured in such a way that a part in the vicinity of the top end of the stick-shaped component 1 on which the balloons 5 and 6 are placed can be rotated on the axis of the stick-shaped component 1 by a rotary unit which is composed of a gear, a rotary shaft, a motor, and so on, the rotary unit being not shown in the drawings.

Besides, a reference numeral 20 in FIG. 2 denotes the luminal wall surface, and a reference numeral 20a in FIG. 2 denotes a diseased region on the luminal wall surface (or the target region for sustained release of the optical clearing agent).

A procedure for performing sustained release of optical clearing agent to a target region for sustained release of optical clearing agent (which is the diseased region 20a on the luminal wall surface 20 in this case) using the device for sustained release of optical clearing agent of the first embodiment having such a configuration is explained using FIG. 2.

As described above, the surface of the luminal wall surface 20 is covered with body fluid. Also, there exists much body fluid on the upper layer of a living tissue required to become transparent, also on the inside of the luminal wall surface 20. If much body fluid mixes with an optical clearing agent, the optical clearing agent is diluted, so that the function of the optical clearing agent making the living tissue transparent is deteriorated and penetration of the optical clearing agent into the living tissue required to become transparent is retarded. In order to shorten necessary time for obtaining the optical clearing effect by sustained release of the optical clearing agent to the luminal wall surface 20, the living tissue being required to become transparent, body fluid existing on the surface of and on the inside of the luminal wall surface 20 has to be reduced to the utmost so that the optical clearing agent easily penetrates into the living tissue required to become transparent.

Accordingly, body fluid on the surface of and on the inside of the diseased region 20a on the luminal wall surface 20 is reduced before sustained release of the optical clearing agent, the diseased region 20 being required to become transparent.

The device for sustained release of optical clearing agent is inserted into the lumen while the balloons 5 and 6 are not being inflated. And then, the top end which is provided with the balloons 5 and 6 is moved to be located at the position of the diseased region 20a of the luminal wall surface 20. Next, the stick-shaped component 1 is rotated a predetermined amount through the rotary unit which is not shown in the drawings so that the body-fluid absorbing component 8 is made to face the diseased region 20a of the luminal wall surface 20 as shown in FIG. 2A, the diseased region 20a being a target region for sustained release of optical clearing agent.

Next, gas (or liquid) is infused into the balloon 6 through the aperture 3a of the supplying passage 3 connecting with the unit for supplying and discharging gas or liquid which is not shown in the drawings, to inflate the balloon 6. As a result, the balloon 6 presses the body-fluid absorbing component 8 to the diseased region 20a of the luminal wall surface 20 while the balloon 6 is being deformed, as shown in FIG. 2B. As a result, the body fluid on the surface of and on the inside of the diseased region 20a of the luminal wall surface 20 is absorbed by the body-fluid absorbing component 8.

After the body fluid is sufficiently absorbed to be removed from the surface of and the inside of the diseased region 20a of the luminal wall surface 20, the gas (or liquid) in the balloon 6 is discharged through the aperture 3a of the supplying passage 3 connecting with the unit for supplying and discharging gas or liquid, the unit for supplying and discharging gas or fluid being not shown in the drawings, so that the balloon 6 is deflated. As a result, the body-fluid absorbing component 8 moves away from the diseased region 20a of the luminal wall surface 20.

Next, the part in the vicinity of the top end of the stick-shaped component 1 is rotated 180 degrees by the rotary unit which is not shown in the drawings so that the optical clearing agent holding component 7 is made to face the diseased region 20a of the luminal wall surface 20, as shown in FIG. 2C.

Next, gas (or liquid) is infused into the balloon 5 through the aperture 2a of the supplying passage 2 connecting with a unit for supplying and discharging gas or liquid which is not shown in the drawings, to inflate the balloon 5. As a result, the balloon 5 presses the optical clearing agent holding component 7 to the diseased region 20a of the luminal wall surface 20 while the balloon 5 is being deformed, as shown in FIG. 2D. As a result, the optical clearing agent held by the optical clearing agent holding component 7 is sustainedly released to the diseased region 20a of the luminal wall surface 20.

The optical clearing agent gradually penetrates into the inside of the diseased region 20a of the luminal wall surface 20 by sustained release of optical clearing agent to the diseased region 20a on the luminal wall surface 20, whereas body fluid existing on the inside of the diseased region 20a of the luminal wall surface 20 soaks to enter the optical clearing agent holding component 7. As described above, the function of the optical clearing agent making living tissue transparent deteriorates when a considerable amount of body fluid enters the optical clearing agent holding component 7 to mix with the optical clearing agent.

Accordingly, in a process in the middle of the sustained release of the optical clearing agent to the diseased region 20a on the luminal wall surface 20, the gas (or liquid) in the balloon 5 is discharged through the aperture 2a of the supplying passage 2 connecting with the unit for supplying and discharging gas or liquid which is not shown in the drawings so that the balloon 5 is deflated to separate the optical clearing agent holding component 7 from the diseased region 20a of the luminal wall surface 20. And then, the stick-shaped component 1 is rotated 180 degrees by the rotary unit which is not shown in the drawings to make the body-fluid absorbing component 8 face the diseased region 20a of the luminal wall surface 20 as shown in FIG. 2A. And, absorption of body fluid soaking out of the diseased region 20a of the luminal wall surface 20 by the body-fluid absorbing component 8 and sustained release of the optical clearing agent to the diseased region 20a of the luminal wall surface 20 by the optical clearing agent holding component 7 are repeated. When a living tissue on the inside of the diseased region 20a of the luminal wall surface 20 becomes as transparent as desired, the sustained release of the optical clearing agent is finished.

After the completion of the sustained release of the optical clearing agent, gas (or liquid) in the balloon 5 is discharged through the aperture 2a of the supplying passage 2 connecting with the unit for supplying and discharging gas or liquid which is not shown in the drawings so that the balloon 5 is deflated to move away from the diseased region 20a of the luminal wall surface 20 in which the living tissue has been made transparent. Next, the device for sustained release of optical clearing agent is moved to be located at a position far away from the diseased region 20a of the luminal wall surface 20. As a result, it is possible to diagnose or treat the transparent living tissue existing in the diseased region 20a of the luminal wall surface 20.

In the case where the transparent living tissue is returned into its original state in which the living tissue is uncleared after diagnosis or treatment of the transparent living tissue existing in the diseased region 20a of the luminal wall surface 20 is finished, the stick-shaped component 1 is pulled out of the living body temporarily. And then, a stick-shaped component 1 including an optical clearing effect-cancelling agent holding component 13 is inserted into the lumen, the optical clearing effect-cancelling agent holding component 13 being fixed on a balloon which is configured in the same manner as the balloons 5 and 6, the optical clearing effect-cancelling agent holding component 13 being composed of a sponge-like component or a pouch-shaped component 12 the surface of which has minute holes for example, and the optical clearing effect-cancelling agent holding component 13 holding saline inside. And, the balloon is inflated to press the optical clearing effect-cancelling agent holding component 13 holding the saline to the diseased region 20a of the luminal wall surface 20 in which the living tissue made transparent exists and to make the optical clearing effect-cancelling agent holding component 13 come into contact with the diseased region 20a of the luminal wall surface 20, with the same procedure as explained above using FIGS. 2C and 2D, and then the saline is sustainedly released. The optical clearing agent in the living tissue is exchanged for the saline, with the result that the living tissue having been made transparent is returned into its original state in which the living tissue is uncleared.

According to the device for sustained release of optical clearing agent of the first embodiment, the device of the first embodiment includes: the stick-shaped component 1 which has the two supplying passages 2 and 3 for supplying gas or liquid inside and which has the apertures 2a and 3a of the supplying passage 2 and 3 at the positions along the circumference of the lateral surface in the vicinity of the top end of the stick-shaped component 1; the at least two pouch-shaped elastic components 5 and 6 which are placed at positions along the circumference of the lateral surface in the vicinity of the top end of the stick-shaped component 1 respectively to cover the apertures 2a and 3a of the supplying passages 2 and 3 respectively and which can be controlled to inflate or deflate in accordance with an amount of inflow of or outflow of gas or liquid; the optical clearing agent holding component 7 which is fixed on the surface of the first pouch-shaped elastic component 5, which holds the optical clearing agent, and which is pressed to sustainedly release the optical clearing agent to the outside; and the body-fluid absorbing component 8 which is fixed on the surface of the second pouch-shaped elastic component 6 and which absorbs body fluid from a target region for sustained release of optical clearing agent or dehydrates the target region for sustained release of optical clearing agent by osmotic pressure. As a result, the optical clearing agent holding component 7 can sustainedly release the optical clearing agent to the luminal wall surface 20 while an amount of body fluid existing in a surface layer on the inside of the luminal wall surface 20 is being reduced to the utmost by removing body fluid adhering to the surface of the luminal wall surface 20 by the body-fluid absorbing component 8. As a result, it is possible to reduce an amount of body fluid that mixes with the optical clearing agent to the utmost, so that it is possible to shorten time which the optical clearing agent needs to penetrate into a living tissue that is required to become transparent on the inside of the luminal wall surface 20.

In addition, according to the device for sustained release of optical clearing agent of the first embodiment, the body-fluid absorbing component 8 and the optical clearing agent holding component 7 are placed at positions along the circumference of the lateral surface in the vicinity of the top end of the stick-shaped component 1, respectively. As a result, absorption of body fluid by the body-fluid absorbing component 8 and sustained release of the optical clearing agent by the optical clearing agent holding component 7 can be changed to each other to be performed respectively without a process of inserting the stick-shaped component 1 into or pulling the stick-shaped component 1 out of the living body by rotating on the axis of the stick-shaped component 1 the part in the vicinity of the top end of the stick-shaped component 1 on which the body fluid absorbing component 8 and the optical clearing agent holding component 7 are placed, so that it becomes possible to reduce a physical burden on the living tissue and a work burden to the utmost.

In addition, according to the device for sustained release of optical clearing agent of the first embodiment, the optical clearing agent holding component 7 and the body-fluid absorbing component 8 are fixed on the first pouch-shaped elastic component 5 and the second pouch-shaped elastic component 6, respectively, and the first pouch-shaped elastic component 5 and the second pouch-shaped elastic component 6 are inflated to be capable of pressing the optical clearing agent holding component 7 and the body-fluid absorbing component 8 to a target region of the luminal wall surface 20 respectively so that the optical clearing agent holding component 7 and the body-fluid absorbing component 8 can come into contact with the target region of the luminal wall surface 20. As a result, the optical clearing agent can be stably given to also a target region existing in the opposite direction to the direction of gravity, and, in addition, it is possible to stably remove body fluid.

Accordingly, the device for sustained release of optical clearing agent of the first embodiment makes it possible to shorten necessary time for obtaining the optical clearing effect by an optical clearing agent to the utmost with a physical burden on a living body and a work burden reduced. In addition, the device for sustained release of optical clearing agent of the first embodiment makes it possible to stably apply an optical clearing agent to also a target region to be applied the optical clearing agent which exists in the opposite direction to the direction of gravity.

Also, according to the device for sustained release of optical clearing agent of the first embodiment, the part in the vicinity of the top end of the stick-shaped component 1, which is provided with the two pouch-shaped elastic components 5 and 6, is configured to be capable of rotating on the axis of the stick-shaped component 1. As a result, absorption of body fluid by the body-fluid absorbing component 8 and sustained release of the optical clearing agent by the optical clearing agent holding component 7 can be changed to each to be performed respectively other without inserting or pulling the stick-shaped component 1 into or out of a living body, so that the effect of reducing a physical burden on the living body and a work burden to the utmost can be realized.

Second Embodiment

Figure 3A:
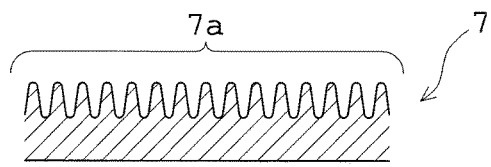
FIGS. 3A to 3E are explanatory views showing a device for sustained release of optical clearing agent of the second embodiment according to the present invention.
Figure 3B:
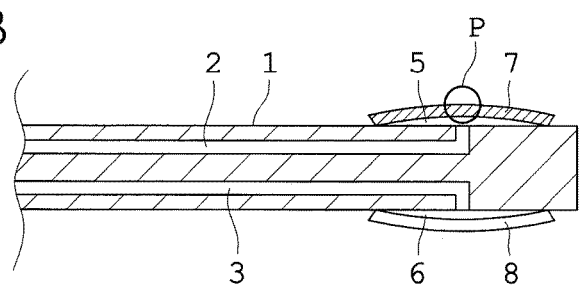
Figure 3C:
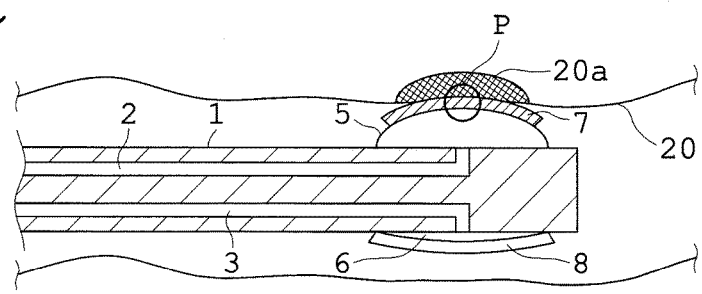
Figure 3D:
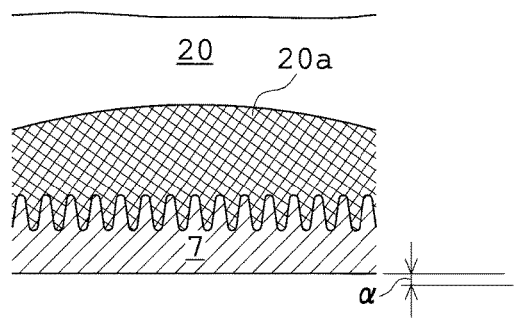
Figure 3E:
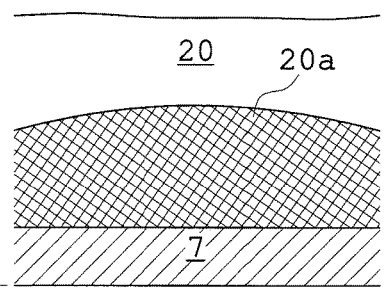

FIGS. 3A to 3C are explanatory views showing a device for sustained release of optical clearing agent of the second embodiment according to the present invention, FIG. 3A is a partially enlarged cross-sectional view showing the surface shape of the optical clearing agent holding component 7, FIG. 3B is a view showing an area which the optical clearing agent holding component 7 for the device for sustained release of optical clearing agent of the second embodiment shown in FIG. 3A occupies, FIG. 3C is a view showing a state in which the optical clearing agent holding component 7 is pressed to a target region for sustained release of optical clearing agent so that the optical clearing agent holding component 7 comes into contact with the target region, FIG. 3D is a view showing: the shape of the pressed contact surface of the target region for sustained release of optical clearing agent in the range of the area shown in FIG. 3C; and a position in the direction in which the optical clearing agent holding component 7 is pressed to come into contact with the target region, when the optical clearing agent holding component 7 is pressed to the target region to come into contact with the target region through the device for sustained release of optical clearing agent of the second embodiment, and FIG. 3E is a view showing one example for comparison with the optical clearing agent holding component 7 shown in FIG. 3D and showing: the shape of the pressed contact surface of the target region for sustained release of optical clearing agent in the range of the area shown in FIG. 3C; and a position in the direction in which an optical clearing agent holding component 7 having a smooth surface is pressed to come into contact with the target region, when the optical clearing agent holding component 7 having a smooth surface is pressed to the target region to come into contact with the target region.

A device for sustained release of optical clearing agent of the present embodiment not only has the constitutions of the device of the first embodiment shown in FIG. 1 but also has a constitution in which innumerable protuberances 7a are formed on the surface of the optical clearing agent holding component 7, as shown in FIG. 3A. Besides, a sign P denoting a part that is surrounded by a circle in FIG. 3B corresponds to a range of the part of the optical clearing agent holding component 7 which is enlarged to be shown in FIG. 3A.

The other constitutions of the present embodiment are approximately equal to those of the device for sustained release of optical clearing agent of the first embodiment shown in FIGS. 1A to 1D.

Now, the contact shape of the diseased region 20a of the luminal wall surface 20 and the position of the optical clearing agent holding component 7 in the direction of the press of the diseased region 20a of the luminal wall surface 20 in the range P are explained using FIGS. 3D and 3E in a case where the optical clearing agent holding component 7 of the present embodiment including the innumerable protuberances 7a on its surface is used and in a case where an optical clearing agent holding component 7 having a smooth surface is used as a comparative example, when the optical clearing agent holding component 7 is pressed to the diseased region 20a of the luminal wall surface 20 to come into contact with the diseased region 20a of the luminal wall surface 20 as shown in FIG. 3C.

In the case where the optical clearing agent holding component 7 of the comparative example having a smooth surface is pressed to the diseased region 20a of the luminal wall surface 20 to come into contact with the diseased region 20a of the luminal wall surface 20, the area of the contact surface of the diseased region 20a of the luminal wall surface 20 with the optical clearing agent holding component 7 is limited to the area of a part over which the flat surface of the diseased region 20a of the luminal wall surface 20 comes into contact with the flat surface of the optical clearing agent holding component 7, as shown in FIG. 3E. As a result, the surface area of the diseased region into which the optical clearing agent penetrates is also limited. In addition, even though the optical clearing agent holding component 7 is pressed to the diseased region 20a with the whole of the smooth surface of the optical clearing agent holding component 7, it is difficult to put a position of the optical clearing agent holding component 7 in the direction of the press of the diseased region 20a on the inside of the diseased region 20a of the luminal wall surface 20.

On the other hand, in the case where the optical clearing agent holding component 7 including the innumerable protuberances 7a on its surface as in the device for sustained release of optical clearing agent of the second embodiment is pressed to the diseased region 20a of the luminal wall surface 20 to come into contact with the diseased region 20a of the luminal wall surface 20, the respective protuberances 7a are pressed into the surface of the diseased region 20a of the luminal wall surface 20, to deform the surface of the diseased region 20a into a bumpy surface corresponding to the bums 7a of the optical clearing agent holding component 7, as shown in FIG. 3D. As a result, the surface area of the diseased region 20a of the luminal wall surface 20 into which the optical clearing agent penetrates is remarkably increased in the second embodiment to be much larger than that in the comparable example. In addition, it is possible to put the optical clearing agent holding component 7 on the inside of the diseased region 20a of the luminal wall surface 20 all the more because the surface of the diseased region 20a of the luminal wall surface 20 is deformed into a bumpy surface by the protuberances 7a of the optical clearing agent holding component 7 as shown with a sign a in FIG. 3D. As a result, the distance between: the optical clearing agent; and a living tissue existing on the inside of the diseased region 20a of the luminal wall surface 20 and being required to become transparent can be shortened.

As described above, the device for sustained release of optical clearing agent of the second embodiment: makes it possible to apply more optical clearing agent to a target region for sustained release of the optical clearing agent; and, in addition, makes it possible to shorten the distance to a living tissue that exists on the inside of the target region for sustained release into which the optical clearing agent penetrates and that is required to become transparent. As a result, it is possible to remarkably shorten necessary time for making the living tissue transparent, the living tissue: existing on the inside of the target region for sustained release of optical clearing agent; and being required to become transparent.

The other operation effects of the device for sustained release of optical clearing agent of the second embodiment are approximately equal to those of the device for sustained release of optical clearing agent of the first embodiment.

Third Embodiment

Figure 4:
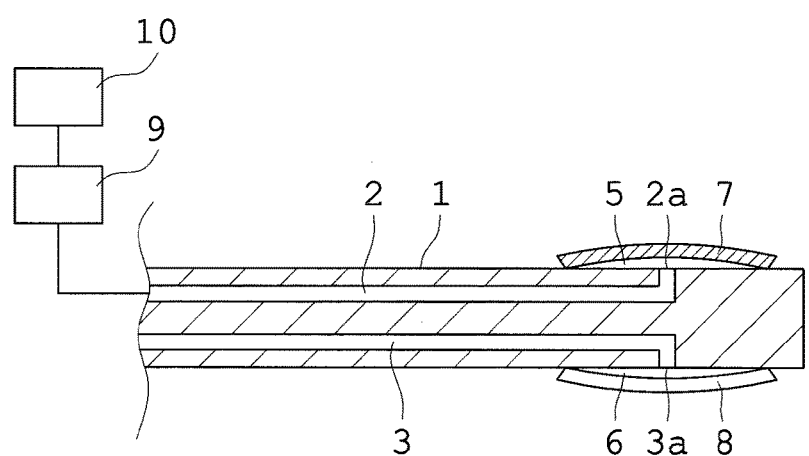
FIG. 4 is an explanatory view schematically showing a sketchy structure of a device for sustained release of optical clearing agent of a third embodiment according to the present invention.

FIG. 4 is an explanatory view schematically showing a sketchy structure of a device for sustained release of optical clearing agent of a third embodiment according to the present invention.

A device for sustained release of optical clearing agent of the present embodiment not only has the constitutions of the first embodiment shown in FIG. 1 but also includes a temperature adjusting apparatus 10 which is used as one of penetration-rate adjusting element that increase a penetration rate of an optical clearing agent held by the optical clearing agent holding component 7, as shown in FIG. 4. Besides, the numeral reference 9 in FIG. 4 denotes a unit for supplying and discharging gas or liquid which is omitted in FIG. 1 and for which a pump is used. Besides, a unit for supplying and discharging gas or liquid which is the same as the unit 9 is connected with also the supplying passage 3, but the same unit for supplying and discharging gas or liquid as the unit 9 is omitted also in FIG. 4.

The temperature adjusting apparatus 10 heats gas (or liquid) supplied to the pouch-shaped elastic component 5 to a predetermined temperature. Heat caused by the heating is conveyed through the pouch-shaped elastic component 5 to the optical clearing agent holding component 7, so that a penetration rate of an optical clearing agent held by the optical clearing agent holding unit 7 is increased.

Besides, with respect to another penetration-rate adjusting element for performing adjustment to increase a penetration rate of the optical clearing agent held by the optical clearing agent holding component 7, penetration-rate accelerating agent may be mixed with the optical clearing agent held by the optical clearing agent holding component 7.

The other constitutions of the present embodiment are approximately equal to those of the device for sustained release of optical clearing agent of the first embodiment shown in FIG. 1.

According to the device for sustained release of optical clearing agent of the third embodiment, gas or liquid which is heated to a predetermined temperature by the temperature adjusting apparatus 10 is supplied into the balloon 5 through the aperture 2a of the supplying passage 2 connecting with the unit 9 for supplying and discharging gas or liquid, so that the balloon 5 is inflated and heat of the heated gas or liquid in the balloon 5 heats the optical clearing agent held by the optical clearing agent holding component 7. As a result, a penetration rate of the optical clearing agent is increased.

And, the balloon 5 is inflated to press the optical clearing agent holding component 7 to the diseased region 20a of the luminal wall surface 20 so that the optical clearing agent holding component 7 comes into contact with the diseased region 20a of the luminal wall surface 20 as shown in FIG. 2D, with the optical clearing agent 7 holding the optical clearing agent the penetration rate of which is improved. As a result, the optical clearing agent the penetration rate of which is increased is sustainedly released from the optical clearing agent holding component 7.

The optical clearing agent the penetration rate of which is increased accelerates dehydration of body fluid existing on the inside of the diseased region 20a of the luminal wall surface 20. Accordingly, the surface of the optical clearing agent holding component 7 is configured to discharge the optical clearing agent to the outside but not to conduct body fluid. And, body fluid is dehydrated from the inside of the diseased region 20a of the luminal wall surface 20 by the optical clearing agent flowing out through the surface of the optical clearing agent holding component 7, the body fluid flowing out from the inside of the diseased region 20a of the luminal wall surface 20 is absorbed by the body-fluid absorbing component 8 afterward, and then the optical clearing agent holding component 7 is again pressed to the diseased region 20a of the luminal wall surface 20 to come into contact with the diseased region 20a of the luminal wall surface 20 again when the diseased region 20a of the luminal wall surface 20 has a small amount of body fluid. As a result, it is become easy for the optical clearing agent flowing out of the optical clearing agent holding component 7 to penetrate into a living tissue that exists on the inside of the diseased region 20a of the luminal wall surface 20 and that is required to become transparent. As a result, it is possible to shorten necessary time for making a living tissue transparent all the more, the living tissue existing on the inside of the diseased region 20a of the luminal wall surface 20 and being required to become transparent.

Also, according to the device for sustained release of optical clearing agent of the third embodiment, the penetration-rate adjusting element is composed of the temperature adjusting apparatus 10 that heats gas or liquid supplied to the pouch-shaped elastic component 5, so that it becomes easy to adjust an extent of shortening of necessary time for making a living tissue transparent, the living tissue being existing on the inside of the diseased region 20a of the luminal wall surface 20 and being required to become transparent.

In addition, in the device for sustained release of optical clearing agent of the third embodiment, a penetration-rate accelerating agent is used as the penetration-rate adjusting element, and the penetration-rate accelerating agent is mixed with the optical clearing agent held by the optical clearing agent holding component 7. As a result, it is possible to shorten necessary time for making a living tissue transparent all the more, the living tissue existing on the inside of the diseased region 20a of the luminal wall surface 20 and being required to become transparent.

The other operation effects of the device for sustained release of optical clearing agent of the third embodiment are approximately equal to those of the device for sustained release of optical clearing agent of the first embodiment.

Fourth Embodiment

Figure 5A:
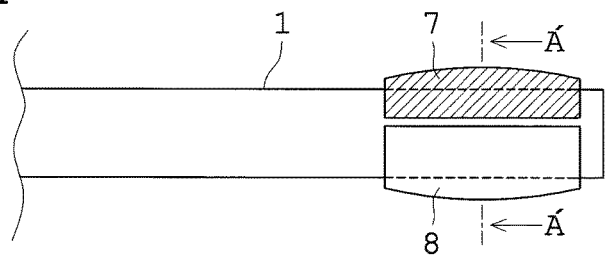
FIGS. 5A to 5C are explanatory views schematically showing a sketchy structure of a device for sustained release of optical clearing agent of the fourth embodiment according to the present invention.
Figure 5B:
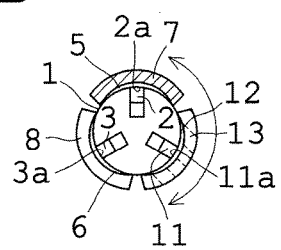
Figure 5C:
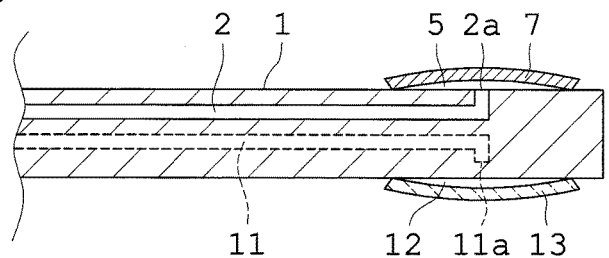
Figures 6A, 6B, 6C, 6D, 6E, 6F:
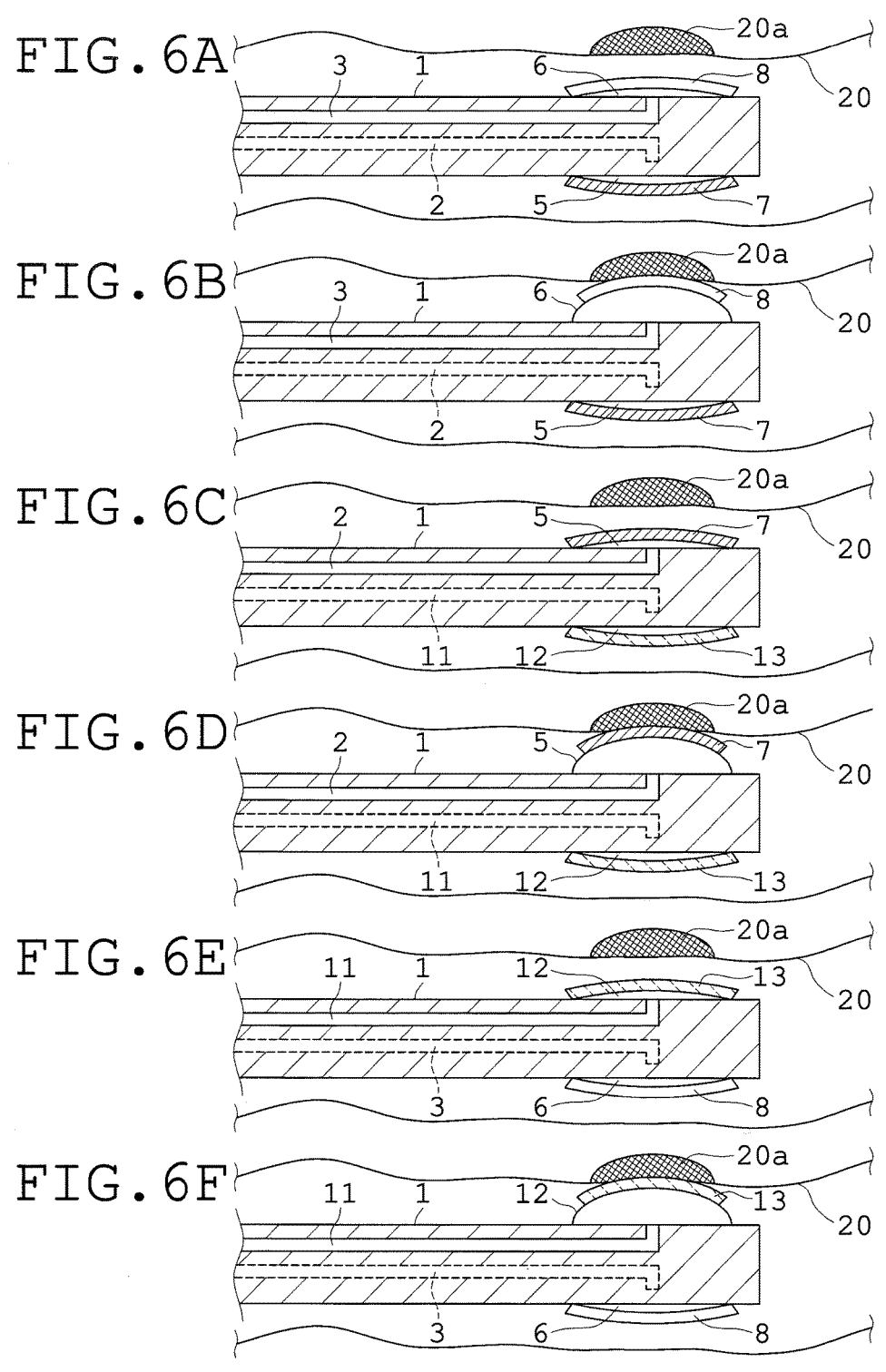

FIGS. 5A to 5C are explanatory views schematically showing a sketchy structure of a device for sustained release of optical clearing agent of the fourth embodiment according to the present invention, FIG. 5A is a side view showing an appearance of a state in which the pouch-shaped elastic components are not inflated, FIG. 5B is a cross-sectional view taken along a line A'-A' in FIG. 5A, and FIG. 5C is a cross-sectional view taken in the direction parallel to the plane of the paper sheet showing FIG. 5A. FIGS. 6A to 6F are explanatory views showing an example of a procedure for sustained release of optical clearing agent with the device for sustained release of optical clearing agent of the fourth embodiment according to the present invention while FIGS. 6B to 6F are being illustrated as a cross-sectional view taken in the direction parallel to the plane of paper sheet showing FIG. 6A, FIG. 6A is a view showing a state in which: the device for sustained release of optical clearing agent is inserted into a lumen with none of the pouch-shaped elastic components inflated; and then the position adjustment for body-fluid absorbing component is performed so that the body-fluid absorbing component faces a target region for sustained release of optical clearing agent, FIG. 6B is a view showing a state in which the second pouch-shaped elastic component is inflated from the state shown in FIG. 6A to press the body-fluid absorbing component to the target region so that the body-fluid absorbing component comes into contact with the target region, FIG. 6C is a view showing a state in which: the second pouch-shaped elastic component is deflated from the state shown in FIG. 6B; and then a part in the vicinity of the top end of the stick-shaped component is rotated on the axis of the stick-shaped component so that the optical clearing agent holding component faces the target region, FIG. 6D is a view showing a state in which the first pouch-shaped elastic component is inflated from the state shown in FIG. 6C to press the optical clearing agent holding component to the target region so that the optical clearing agent holding component comes into contact with the target region, FIG. 6E is a view showing a state in which: the first pouch-shaped elastic component is deflated from the state shown in FIG. 6D; and then the part in the vicinity of the top end of the stick-shaped component is rotated on the axis of the stick-shaped component so that the optical clearing effect-cancelling agent holding component faces the target region, and FIG. 6F is a view showing a state in which the third pouch-shaped elastic component is inflated from the state shown in FIG. 6E to press the optical clearing effect-cancelling agent holding component to the target region so that the optical clearing effect-cancelling agent holding component comes into contact with the target region.

A device for sustained release of optical clearing agent of the present embodiment includes not only the components shown in FIG. 1 but also an expandable pouch-shaped elastic component 12 and an optical clearing effect-cancelling agent holding component 13, as shown in FIGS. 5A to 5C.

The stick-shaped component 1 includes not only the supplying passages 2 and 3 but also a supplying passage 11 for supplying gas or liquid, the supplying passages 2, 3, and 11 being formed on the inside of the stick-shaped component 1.

Also, as shown in FIG. 5B, the stick-shaped component 1 includes apertures 2a, 3a, and 11a of the supplying passages 2, 3, and 11 which are formed at positions along the circumference of the lateral surface in the vicinity of the top end of the stick-shaped component 1 respectively.

The supplying passage 11 is connected with the unit for supplying and discharging gas or liquid which is not shown in the drawings and for which a pump is used, as well as the supplying passages 2 and 3.

The pouch-shaped elastic component 12 is composed of a balloon for example and is placed at a position along the circumference of the lateral surface in the vicinity of the top end of the stick-shaped component 1 while the position of the pouch-shaped component 12 placed is being different from the positions of the balloons 5 and 6 placed respectively, and the pouch-shaped elastic component 12 covers the aperture 11a of the supplying passage 11, as shown in FIGS. 5B and 5C.

And, gas or liquid is supplied to the inside of the balloon 12 through the aperture 11a of the supplying passage 11 to expand (inflate) the balloon 12, the supplying passage 11 being connected with the unit for supplying and discharging the gas or the liquid which is not shown in the drawings. And, gas or liquid is discharged from the inside of the balloon 12 through the aperture 11a of the supplying passage 11 to contract (deflate) the balloon 12. Accordingly, the balloon 12 is configured to be capable of being controlled to inflate or deflate in accordance with an amount of inflow of or outflow of gas or liquid.

The optical clearing effect-cancelling agent holding component 13 holds an optical clearing effect-cancelling agent like a saline inside, the optical clearing effect-cancelling agent being used for retuning a living tissue having been made transparent into its original state in which the living tissue is uncleared. And, the optical clearing effect-cancelling agent holding component 13 is pressed to sustainedly release the optical clearing effect-cancelling agent to the outside. For example, the optical clearing effect-cancelling agent holding component is made as: a sponge-like component; or a pouch-shaped component the surface of which is provided with minute holes, and the optical clearing effect-cancelling agent holding component 13 is fixed on the surface of the balloon 12.

The other constitutions of the present embodiment are approximately equal to those of the device for sustained release of optical clearing agent which is shown in FIG. 1.

The device for sustained release of optical clearing agent of the fourth embodiment having such a configuration makes it possible to perform processes: from sustained release of optical clearing agent to the diseased region 20a of the luminal wall surface 20 which is a target region for sustained release of optical clearing agent; to sustained release of optical clearing effect-cancelling agent to the diseased region 20a of the luminal wall surface 20 for returning a living tissue having been made transparent into its original uncleared state of the living tissue, without pulling out the stick-shaped component 1 form the living body. The procedure for performing these processes is explained using FIG. 6.

The procedure for performing sustained release of an optical clearing agent to the diseased region 20a of the luminal wall surface 20 in the present embodiment is approximately equal to that in the device for sustained release of optical clearing agent of the first embodiment shown in FIG. 2.

Specifically, the device for sustained release of optical clearing agent is inserted into a lumen without inflating the balloons 5, 6, and 12. And, the top end including the balloons 5, 6, and 12 is moved to be located at a position of the diseased region 20a of the luminal wall surface 20. Next, the stick-shaped component 1 is rotated a predetermined amount by the rotary unit which is not shown in the drawings so that the body-fluid absorbing component 8 faces the diseased region 20a of the luminal wall surface 20 which is a target region for sustained release of optical clearing agent, as shown in FIG. 6A.

Next, gas (or liquid) is supplied to the inside of the balloon 6 through the aperture 3a of the supplying passage 3 connecting with the unit for supplying and discharging gas or liquid which is not shown in the drawings, to inflate balloon 6. As a result, the balloon 6 is deformed to press the body-fluid absorbing component 8 to the diseased region 20a of the luminal wall surface 20 so that the body-fluid absorbing component 8 comes into contact with the diseased region 20a of the luminal wall surface 20, as shown in FIG. 6B. As a result, body fluid from the surface of or the inside of the diseased region 20a is absorbed by the body-fluid absorbing component 8.

After body fluid flowing from the surface of and from the inside of the diseased region 20a of the luminal wall surface 20 is sufficiently absorbed, the gas (or liquid) in the balloon 6 is discharged through the aperture 3a of the supplying component 3 connecting with the unit for supplying and discharging gas or liquid which is not shown in the drawings, to deflate the balloon 6. As a result, the body-fluid absorbing component 8 is separated from the diseased region 20a of the luminal wall surface 20.

Next, the part in the vicinity of the top end of the stick-shaped component 1 is rotated 180 degrees by the rotary unit which is not shown in the drawings, so that the optical clearing agent holding component 7 is made to face the diseased region 20a, as shown in FIG. 6C.

Next, gas (or liquid) is supplied to the inside of the balloon 5 through the aperture 2a of the supplying passage 2a connecting with the unit for supplying and discharging gas or liquid which is not shown in the drawings, to inflate balloon 5. As a result, the balloon 5 is deformed to press the optical clearing agent holding component 7 to the diseased region 20a so that the optical clearing agent holding component 7 comes into contact with the diseased region 20a, as shown in FIG. 6D. As a result, optical clearing agent held by the optical clearing agent holding component 7 is sustainedly released to the diseased region 20a of the luminal wall surface 20.

Besides, the gas (or liquid) in the balloon 5 is discharged through the aperture 2a of the supplying passage 2 connecting with the unit for supplying and discharging gas or liquid which is not shown in the drawings, to deflate the balloon 5, in the middle of the sustained release of the optical clearing agent. As a result, the optical clearing agent holding component 7 is separated from the diseased region 20a of the luminal wall surface 20. And then, the stick-shaped component 1 is rotated 180 degrees by the rotary unit which is not shown in the drawings, so that the body-fluid absorbing component 8 faces the diseased region 20a, as shown in FIG. 6A. And then, absorption of body fluid soaking out of the diseased region 20a of the luminal wall surface 20 by the body-fluid absorbing component 8 and sustained release of the optical clearing agent to the diseased region 20a by the optical clearing agent holding component 7 are repeated. When a living tissue existing on the inside of the diseased region 20a of the luminal wall surface 20 becomes as transparent as desired, the sustained release of the optical clearing agent is finished.

After the sustained release of the optical clearing agent is finished, the gas (or liquid) in the balloon 5 is discharged through the aperture 2a of the supplying passage 2 connecting with the unit for supplying and discharging gas or liquid which is not shown in the drawings, to deflate the balloon 5. As a result, the balloon 5 is separated from the diseased region 20a of the luminal wall surface 20 in which the living tissue has become transparent. Next, the device for sustained release of optical clearing agent is temporarily kept away from the diseased region 20a of the luminal wall surface 20. As a result, it is possible to diagnose or treat the transparent living tissue existing in the diseased region 20a of the luminal wall surface 20.

In the case where the transparent living tissue is returned into its original uncleared state after the diagnosis of or the treatment of the transparent living tissue existing in the diseased region 20a of the luminal wall surface 20 is finished, the device for sustained release of optical clearing agent is inserted into the lumen while the balloons 5, 6, and 12 are not being inflated, and the top end of the stick-shaped component 1 including the balloons 5, 6, and 12 is moved to be located at the position of the diseased region 20a of the luminal wall surface 20. Next, the stick-shaped component 1 is rotated a predetermined amount by the rotary unit which is not shown in the drawings, so that the optical clearing effect-cancelling agent holding component 13 is made to face the diseased region 20a of the luminal wall surface 20 which is a target region for sustained release of optical clearing agent and in which the living tissue having been made transparent exists, as shown in FIG. 6E.

Next, gas (or liquid) is supplied to the inside of the balloon 12 through the aperture 11a of the supplying passage 11 connecting with the unit for supplying and discharging gas or liquid which is not shown in the drawings, to inflate the balloon 12. As a result, the balloon 12 is deformed to press the optical clearing effect-cancelling agent holding component 13 to the transparent diseased region 20a of the luminal wall surface 20 so that the optical clearing effect-cancelling agent holding component 13 comes into contact with the transparent diseased region 20a of the luminal wall surface 20, as shown in FIG. 6F. As a result, saline held by the optical clearing effect-cancelling agent holding component 13 is sustainedly released to the diseased region 20a of the luminal wall surface 20, so that the saline is exchanged for the optical clearing agent in the living tissue and then the living tissue having been put transparent is returned into its original state in which the living tissue is uncleared.

According to the device for sustained release of optical clearing agent of the fourth embodiment, the stick-shaped component 1 includes: the third supplying passage 11 for supplying gas or liquid which is formed on the inside of the stick-shaped component 1; and the aperture 11a of the third supplying passage which is formed at a position along the circumference of the lateral surface in the vicinity of the top end of the stick-shaped component 1, and the device for sustained release of optical clearing agent of the fourth embodiment includes the optical clearing effect-cancelling agent component 13 which is fixed on the surface of the balloon 12, which holds the liquid for returning a living tissue having been made transparent into its original uncleared state, and which is pressed to sustainedly releases the liquid for returning the transparent living tissue into its original uncleared state to the outside, the balloon 12 being placed at the position along the circumference of the lateral surface in the vicinity of the top end of the stick-shaped component to cover the aperture 11a of the third supplying passage while the position of the balloon 12 (the third pouch-shaped elastic component) placed is being different from the places of the balloon 5 (the first pouch-shaped elastic component) and the balloon 6 (the second pouch-shaped elastic component) placed respectively, and the balloon 12 being capable of being controlled to expand or contract in accordance with an amount of inflow of or outflow of gas or liquid. As a result, it is possible: not only to shorten necessary time for the optical clearing agent to penetrate into a living tissue that exists on the inside of the diseased region of the luminal wall surface 20 and that is required to become transparent, by sustainedly releasing the optical clearing agent in a manner of by the optical clearing agent holding component 7 after the body-fluid absorbing component 8 reduces an amount of body fluid existing on the surface of the diseased region 20*a* of the luminal wall surface 20 and on the surface layer on the inside of the diseased region 20*a* of the luminal wall surface 20 to the utmost; but also to stably give the optical clearing effect-cancelling agent to also a target region for sustained release which exists in the opposite direction to the direction of gravity without inserting the stick-shaped component 1 into and pulling out the stick-shaped component 1 from the living body in also a process of opacifying the living tissue which was made transparent. As a result, it is possible to reduce a physical burden on the living body and a work burden all the more.

The other operation effects of the device for sustained release of optical clearing agent of the present embodiment are approximately equal to those of the device for sustained release of optical clearing agent of the first embodiment.

Fifth Embodiment

Figure 7:
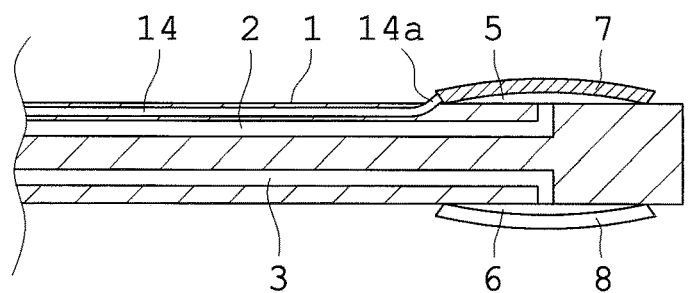
FIG. 7 is an explanatory view schematically showing a sketchy structure of a device for sustained release of optical clearing agent of the fifth embodiment according to the present invention.
Figure 8:
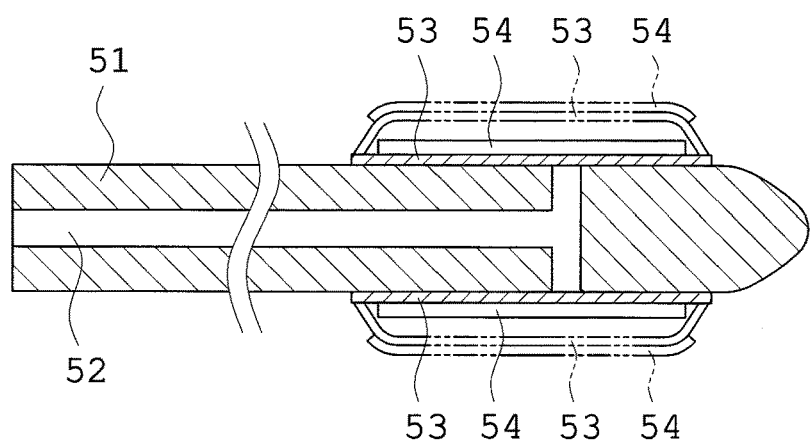
FIG. 8 is a cross-sectional view showing one example of an agent-applying instrument disclosed in Japanese Patent Kokai No. 2008-188212.

FIG. 7 is an explanatory view schematically showing a sketchy structure of a device for sustained release of optical clearing agent of the fifth embodiment according to the present invention.

A device for sustained release of optical clearing agent of the present embodiment not only has the constitutions of the first embodiment shown in FIG. 1 but also has a constitution in which the stick-shaped component 1 further includes a supplying passage 14 for supplying optical clearing agent which connects with the optical clearing agent holding component 7 through a connection part 14*a*.

The supplying passage 14 is connected with a unit for supplying and discharging an optical clearing agent which is not shown in the drawings and for which a pump or the like is used.

The other constitutions of the present embodiment are approximately equal to those of the device for sustained release of optical clearing agent of the first embodiment.

In the case where an amount of an optical clearing agent necessary for making the diseased region 20*a* transparent exceeds an amount of the optical clearing agent capable of being held by the optical clearing agent holding component 7, another sustained release of the optical clearing agent is needed.

In the case where another sustained release of the optical clearing agent is performed using the device for sustained release of optical clearing agent of the first to fourth embodiments, the stick-shaped component 1 has to be inserted into a living body again, after the stick-shaped component 1 is pulled out from the living body temporarily and then the optical clearing agent component 7 is replenished with an optical clearing agent.

However, according to the device for sustained release of optical clearing agent of the fifth embodiment, the stick-shaped component 1 further includes the supplying passage 14 for supplying optical clearing agent which connects with the optical clearing agent holding component 7, so that it becomes possible to control an amount of optical clearing agent sustainedly released to a target region into a suitable amount. As a result, even in the case where an amount of the optical clearing agent necessary for making a living tissue existing on a target region transparent exceeds an amount of the optical clearing agent capable of being held by the optical clearing agent holding component 7 for the device for sustained release of optical clearing agent and consequently another amount of the optical clearing agent is needed, it is possible to properly replenish the optical clearing agent holding component 7 with another amount of optical clearing agent as necessary through the supplying passage 14 for supplying optical clearing agent, so that it is possible to finish the process of making the living tissue transparent without pulling out the stick-shaped component 1 from the living body.

The embodiments of the device for sustained release of optical clearing agent according to the present invention have been explained up to now. However, device for sustained release of optical clearing agent according to the present invention are not limited to the constitutions for above-described embodiments, and the characteristic constitutions of the respective embodiments may be optionally combined with one another. Also, for example, the pouch-shaped elastic components are not limited to the balloons, and any component expanding into a shape of a pouch and having elasticity may be used as a pouch-shaped elastic component. Also, the device for sustained release of optical clearing agent that were explained in the above-described explanations about the embodiments of the present invention may be configured to be integrated with the top end of an endoscope or may be configured to be integrated with an instrument for endoscopic surgery like a extractor which is used together with an endoscope.

A device for sustained release of optical clearing agent according to the present invention and an endoscope and an instrument for endoscopic surgery which have the same are useful for every field in which a diseased region existing in the opposite direction to the direction of gravity has to be given an optical clearing agent while the optical clearing agent is being kept on the diseased region and has to be diagnosed or treated immediately after giving the optical clearing agent to the diseased region.

What is claimed is:

1. A method for achieving sustained release of optical clearing agent comprising:
   (a) inserting into a lumen a device for sustained release of optical clearing agent without inflating any of at least two pouch-shaped elastic components of the device, the device comprising:
      a stick-shaped component inside which at least two supplying passages are formed for supplying gas or liquid and which has apertures of the respective supplying passages formed at positions in a vicinity of a top end of the stick-shaped component along a circumference of a lateral surface thereof,
      the at least two pouch-shaped elastic components placed at positions in the vicinity of the top end of the stick-shaped component along the circumference of the lateral surface of the stick-shaped component to cover the respective apertures of the supplying passages respectively;
   (b) moving the device for sustained release of optical clearing agent so that the top end of the stick-shaped component, where the pouch-shaped elastic components are provided, is positioned to a diseased region on a wall surface of the lumen;
   (c) rotating the stick-shaped component via a rotary unit until a body-fluid absorbing component fixed on a surface of a first pouch-shaped elastic component, which is one of the at least two pouch-shaped elastic components, is made to face the diseased region;

(d) infusing gas or liquid into the first pouch-shaped elastic component from the aperture of a first supplying passage, which is one of the at least two supplying passages inside the stick-shaped component, via the first supplying passage, to inflate the first pouch-shaped elastic component;

(e) pressing the body-fluid absorbing component against the diseased region through deformation of the first pouch-shaped elastic component, to make the body-fluid absorbing component absorb body fluid on a surface of and from inside the diseased region;

(f) discharging the gas or fluid from inside the first pouch-shaped elastic component through the aperture of the first supplying passage, to deflate the first pouch-shaped elastic component and detach the body-fluid absorbing component from the diseased region;

(g) rotating the stick-shaped component via the rotary unit until an optical clearing agent holding component fixed on a surface of a second pouch-shaped elastic component, which is one of the at least two pouch-shaped elastic components, is made to face the diseased region;

(h) infusing gas or liquid into the second pouch-shaped elastic component from the aperture of a second supplying passage, which is one of the at least two supplying passages inside the stick-shaped component, via the second supplying passage, to inflate the second pouch-shaped elastic component; and (i) pressing the optical clearing agent holding component against the diseased region through deformation of the second pouch-shaped elastic component, to establish sustained release of optical clearing agent held by the optical clearing agent holding component to the diseased region.

2. The method for achieving sustained release of optical clearing agent according to claim 1, further comprising the steps of:

discharging the gas or fluid from inside the second pouch-shaped elastic component through the aperture of the second supplying passage, to deflate the second pouch-shaped elastic component and detach the optical clearing agent holding component from the diseased region; and repeating steps (c) to (i).

\* \* \* \* \*